United States Patent [19]

Wagner

[11] Patent Number: 4,888,288

[45] Date of Patent: Dec. 19, 1989

[54] VESICLES RESISTANT TO ENZYME LYSIS AND USE THEREOF IN AN ENZYME ASSAY

[75] Inventor: Daniel B. Wagner, Raleigh, N.C.

[73] Assignee: Becton Dickinson and Company, Franklin Lakes, N.J.

[21] Appl. No.: 824,362

[22] Filed: Jan. 30, 1986

[51] Int. Cl.$^4$ ............................................. C12Q 1/42
[52] U.S. Cl. ........................................ 435/21; 264/4; 424/450; 428/402.2; 435/4; 435/177; 435/182; 435/19; 435/7; 436/829; 514/76; 514/77; 514/78
[58] Field of Search ............... 424/450; 435/177, 182, 435/4, 7, 19, 21; 436/829; 514/76–78; 558/169; 428/402.2

[56] References Cited

U.S. PATENT DOCUMENTS

| | | | |
|---|---|---|---|
| 4,221,732 | 9/1980 | Oette et al. | 558/169 |
| 4,480,041 | 10/1984 | Myles et al. | 436/829 |
| 4,485,045 | 11/1984 | Regen | 424/450 |
| 4,619,794 | 10/1986 | Hauser | 424/450 |

OTHER PUBLICATIONS

Rosenthal et al.–Biochimica et Biophysica Acta vol. 218 (1970) pp. 213–220.

*Primary Examiner*—Sam Rosen
*Attorney, Agent, or Firm*—Elliot M. Olstein; Raymond J. Lillie

[57] ABSTRACT

Liposomes are formed from compounds including a phosphonate or phosphinate group instead of a phosphate group. The liposomes bind to enzymes, such as a phospholipase, and such liposomes containing a detectable marker may be used as a substrate in an enzyme immunoassay.

18 Claims, No Drawings

VESICLES RESISTANT TO ENZYME LYSIS AND USE THEREOF IN AN ENZYME ASSAY

This invention relates to vesicles and sacs and to the use thereof. This invention further relates to an assay for a ligand which employs a vesicle or sac as a component thereof.

Vesicles or sacs are generally produced from amphiphilic compounds (compounds having both a hydrophobic portion and hydrophilic portion), with such vesicles or sacs being most commonly produced from lipids; in particular, phospholipids. When the vesicles or sacs are produced from lipids they are most often referred to as liposomes.

As known in the art, such vesicles or sacs may be formed in a manner such as to encapsulate a material in the interior of the sac. Thus, for example, such sacs have been used to encapsulate biologically active materials; for example, a therapeutic drug.

In addition, such sacs have been employed to encapsullate a detectable marker for use in an assay for a ligand. Thus, for example, in an assay for a ligand, the tracer used in the assay may be produced by coupling the ligand or appropriate analog thereof to a sac containing a detectable marker. In such an assay, for example, the tracer and ligand to be determined (analyte) may compete for a limited number of binding sites on a binder for both the tracer and analyte. The amount of tracer which is bound to the binder is inversely proportional to the amount of analyte in the sample. The bound and/or unbound portion of the tracer is determined as a measure of analyte by releasing the marker from the sac.

In such assays, in producing a tracer, it is necessary to conjugate a ligand to the sac containing the detectable marker. It has been found that in many cases such tracers do not have the requisite stability; i.e., after a period of time, the sac deteriorates and/or the ligand does not remain coupled to the sac. In addition, it is necessary to produce and store sacs conjugated to a variety of ligands for use in assays for a variety of analytes.

In accordance with one aspect of the present invention, a sac or vesicle (sometimes referred to as a lipid vesicle) is formed from analogs of phospholipids wherein, in such analogs, the phosphate group is replaced by a phosphonate or phosphinate group. In addition, if the phospholipid normally includes an ester moiety (ester of a fatty acid), the ester linkage is replaced with an ether linkage.

Applicant has found that by utilizing a compound(s) of the type hereinabove described in forming a sac, the sac is not lysed by enzymes which normally lyse sacs formed from phospholipids (for example, phospholipases lyse sacs formed from phospholipids), and in addition, the sacs formed from such analogs are bound by an enzyme, without lysing of the sacs.

Compounds which may be used in producing sacs in accordance with the present invention, may be represented by the following structural formula I:

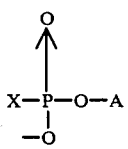

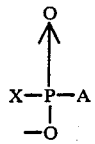

wherein X is a hydrophobic radical and A is a hydrophilic radical.

As representative examples of hydrophobic radicals represented by X in the structural formula, there may be mentioned those having the following structural formula:

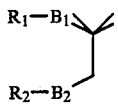

wherein each of $B_1$ and $B_2$ are each either —O— or —$CH_2$— and may be the same or different $R_1$ and $R_2$ are each a substituted or unsubstituted hydrocarbon radical (saturated or unsaturated) having at least 11 carbon atoms and may be the same or different radicals and $R_1$ and $R_2$ may be linked together to form a cyclic compound, and Y is a hydrocarbon radical having from 1–5 carbon atoms, preferably 3 or 4 carbon atoms.

As representative examples of hydrophilic radicals represented by A in the structural formula, there may be mentioned those having the following structural formula:

$(CH_2)_c$—$N^+$—$(R')_3$ wherein c is 2 to 10, and R' is hydrogen or an aliphatic hydrocarbon radical having from 1 to 8 carbon atoms and each may be the same or different.

Radical A is preferably

—$CH_2$—$N^+(CH_3)_3$ or

—$CH_2$—$CH_2$—$N^+H_3$ and X is preferably

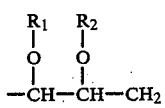

wherein $R_1$ and $R_2$ are as previously defined.

Thus, the preferred compounds are lecithin analogs wherein the phosphate moiety is replaced by a phosphonate or phosphinate moiety and the ester linkage is replaced by an ether linkage.

The compounds of the type hereinabove described are known in the art; for example, Rosenthal, et al, *Rec. Trav. Chim.* 84 (1965) 833; Rosenthal *J. Lipid Res.* 7 (1969) 37; Rosenthal et al *Lipids* 4 (1969) 37; Rosenthal et al *Chem Commun.* (1968) 1504; Rosenthal et al *Biochim., Biophys. Acta* 218 (1970) 213.

The sacs or vesicles, which are formed from a compound as hereinabove described may be produced by procedures generally available in the art for producing sacs or vesicles. For example, the sac or vesicle may be produced by a reverse phase technique wherein the compound or compounds used in producing the sac or vesicle are initially dissolved in an organic phase, followed by addition of an aqueous phase and forming of a homogeneous emulsion. After forming the emulsion, the organic solvent is evaporated to form a gel-like material, and such gel may be converted to a sac or vesicle by agitation or dispersion in an aqueous media such as a buffer solution.

Procedures for producing vesicles or sacs are generally known in the art, and such procedures may be employed for producing a sac or vesicle in accordance with the present invention. As known in the art, the stability of the vesicle is increased by using a material such as cholesterol as one of the components in forming the vesicle. Thus, in forming the liposome, the phospholipid components are replaced with the analogs hereinabove described.

Details with respect to the preparation of sacs are set forth in U.S. Pat. No. 4,241,046; U.S. Pat. No. 4,342,826, and P.C.T. International Publication No. Patent WO 80-01515.

As known in the art, if a material is to be encapsulated in the sac, such material may be encapsulated by including the ing the material in an aqueous solution in which the sac or vesicle is formed. Alternatively, the material may be encapsulated into a previously formed "empty" sac by the procedure described in U.S. application Ser. No. 650,200, filed on Sept. 13, 1984 (Attorney Docket No. P/3521).

In accordance with another aspect of the present invention, a sac of the type hereinabove described, including a detectable marker, may be used in an assay employing a tracer in which an enzyme is used as the label, often referred to as an enzyme assay or an enzyme immunoassay.

In an enzyme assay, the tracer which is employed in the assay is a ligand having an enzyme coupled thereto. The ligand which is employed in producing the tracer is dependent upon the assay which is employed. Thus, for example, if the assay is for an analyte (ligand to be determined) which is an antigen or a hapten, the ligand portion of the tracer may be the analyte or appropriate analog thereof. As used herein, the term "appropriate analog", when referring to an analog of the analyte, means that the analog of the analyte is bound by the binder for the analyte which is used in the assay.

The ligand portion of the tracer may also be an antibody to the analyte. Similarly, if the analyte is an antibody, the ligand portion of the tracer may be an antigen bound by the antibody or an antibody elicited in response to the analyte or the antibody.

In any event, the ligand portion of the tracer is bound by one of the binder or the analyte. Thus, for example, in a so-called "sandwich" assay, the analyte may be bound by the the binder and the tracer bound by the analyte, whereby the amount of the tracer bound to the binder through the analyte is proportional to the amount of analyte in the sample. In an alternative procedure, the binder may be a binder for both the analyte and the ligand portion of the tracer, whereby the amount of tracer bound to the binder is inversely proportional to the amount of analyte in the sample.

In both procedures, there is formed a bound tracer portion and a free (unbound) tracer portion and the presence and/or amount of analyte may be determined by measuring the bound and/or free tracer portion.

In accordance with the present invention, the sacs prepared in accordance with the present invention, and including a detectable marker, are employed as a substrate for the enzyme of the bound and/or free portion of the assay. More particularly, the sacs produced in accordance with the present invention are bound by an enzyme and are not lysed by the enzyme portion of the bound tracer. In this manner the amount of bound and/or free tracer can be determined by measuring detectable marker of the sacs bound to the bound and/or free tracer portion, which measurement provides a measure of analyte.

The marker which is included within the sac for use in an assay may be any one of a wide variety of detectable markers, including but not limited to radioisotopes, chromogens (an absorbing dye and/or a fluorescent material), a luminescent compound, spin labels, etc. Such detectable markers, and the methods for determining the markers are generally known in the art, and no further details in this respect are deemed necessary for a complete understanding of the invention. The preferred types of markers are dyes with a high extinction coefficient such as sulforhodamine B, fluorescent dye such as carboxyfluorescein, and the like.

The assay is generally run in an appropriately buffered aqueous medium which is isotonic with the osmolarity of the sacs. Thus, conditions of temperature, pH and ionic concentrations are controlled to prevent premature rupturing of the sacs. Thus, for example, an aqueous buffered medium is provided which is isotonic with the osmolarity of the sacs, and in general, such a buffer provides a pH in the order of from 5-9.

In the assay, as known in the art, there is produced in the assay a bound tracer portion and a free tracer portion. In a so-called "sandwich" assay, a portion of the tracer becomes bound to the analyte bound to binder, and a portion of the tracer remains free (unbound) in the assay medium. The amount of tracer which becomes indirectly bound to the binder is directly proportional to analyte. In a competitive type of assay, the tracer and analyte compete for binding sites, whereby the amount of tracer which is bound to the binder is inversely proportional to the amount of analyte in the sample. In accordance with the invention, depending on the assay system employed, the amount of sacs which are bound to the bound tracer portion is either directly or inversely proportional to analyte present in the assay medium, whereby analyte can be determined by measuring detectable marker of the sacs bound to the bound and/or free tracer portion produced in the assay.

The sacs may be contacted with the bound and/or free tracer portion prior or subsequent to separation of the bound and free tracer portions. If contacting is effected prior to separation of the bound and free tracer portions, then the sacs which are not bound to the bound tracer portion are separated along with the free tracer portion.

If contacting is effected subsequent to separation of the bound and free tracer portions, then the sacs which are not bound to the bound tracer are separated from the sacs which are bound to the bound tracer.

In accordance with a representative assay procedure, a binder for the analyte is supported on a solid support and the tracer is comprised of a binder for the analyte coupled to an enzyme. In the assay, a sample containing or suspected of containing the analyte is incubated with a binder for the analyte on a solid support and tracer comprised of a binder specific for the analyte coupled to an appropriate enzyme. Sacs, including a detectable marker, of the type hereinabove described may be included in the incubation or may be subsequently added. As a result, analyte is bound by the supported binder; tracer is bound by analyte; and the sacs are bound by the tracer, whereby the amount of sacs which are indirectly bound to the supported binder is directly proportional to the amount of analyte in the sample.

The bound components (sacs bound to tracer bound to analyte bound to supported binder) are separated from the free components (sacs and tracer not bound to the supported binder). The bound sacs are determined by measuring detectable marker which is a measure of the presence and/or amount of analyte in the sample. Such amount is determined by comparing the assay value with those obtained by an identical procedure using known amounts of analyte (analyte standards prepared with known concentrations of analyte), often referred to as a standard curve.

The detectable marker may be determined by rupturing the sacs to release the marker. Alternatively, as described in U.S. application Ser. No. 579,667 in some cases it may be possible to determine the marker without rupturing the sacs. The sacs may be ruptured by changing conditions, such as pH, temperature, ionic concentration, addition of a detergent, which change ruptures the sacs to release marker, which can be measured by procedures known in the art.

Although an assay procedure has been described with respect to a "sandwich" type of assay, it is to be understood that the present invention is also applicable to other assay procedures, such as a competitive assay, wherein analyte and tracer compete for binding sites on a supported or unsupported binder. Sacs including detectable marker of the type hereinabove described are employed in the assay, and detectable marker in the sacs which are bound to the bound tracer portion produced in the assay are determined as a measure of the presence and/or amount of analyte.

The enzyme which is used in producing the tracer is one which is capable of binding the sacs produced in accordance with the invention and one which does not lyse the sacs. As representative examples of a suitable enzyme, there may be mentioned phospholipases.

In accordance with a further aspect of the present invention, there is provided a reagent kit or package for accomplishing an assay for an analyte which includes: (a) a tracer comprised of either the analyte to be assayed or appropriate analog thereof conjugated to an enzyme, or a binder for the analyte conjugated to an enzyme and (b) sacs which include a detectable marker wherein the sac is formed from a compound or compounds having a structural formula I as hereinabove described. The reagent kit or package may also include an appropriate binder, in supported or unsupported form, with such binder being a binder for at least the analyte, and in some cases, the binder is a binder for both the tracer and the analyte. As known in the art, such binder may be either an antibody or an appropriate naturally occurring binder. The components of the kit may be included in the kit of package in separate containers; for example, vials; however, in some cases, one or more of the components may be combined into a single vial. The kit may also include other components such as standards of the analyte (analyte samples having known concentrations of the analyte), known buffers, and the like. Such kit or package may be employed in an assay for an analyte by use of procedures of the type hereinabove described.

The assay and reagent kit of the present invention may be employed for determining a wide variety of analytes, and has particular applicability to those analytes which are generally found in low concentrations in the material to be assayed. As representative examples of such analytes, there may be mentioned: cardiac glycosides, such as digoxin and digitoxin: antiasthmatics, such as theophyllin; antibiotics, such as gentamicin and tobramycin; atineopalastics, such as amethrotrexate; anticonvulsants, such as pheno-barbitol, carbamezapine and valparic acid; antiarrythmics, such as lidocaine and quinidine; hormones, such as T4, T3, hCG, TSH, and various steroids, viral antigens, viral antibodies, etc. These and other analytes should be apparent to those skilled in the art, and no further teachings in this respect are deemed necessary for a full understanding of the invention. It is to be understood that the scope of the present invention is not to be limited to the representative analytes.

As should be apparent, by employing a sac as hereinabove described, in an enzyme assay, it is possible to produce a sac having a detectable marker, which is not conjugated to a ligand. As a result, the sac has increased stability. Moreover, it is not necessary to produce sacs conjugated to different ligands in order to use the sacs in a wide variety of assays. Moreover, by employing a sac containing a detectable marker, there is an amplification of the signal in that a single tracer molecule is capable of releasing a high concentration of detectable marker.

Although the sacs produced in accordance with the present invention are preferably produced in a manner such that the sacs include a detectable marker; in particular, for use in an enzyme assay, it is to be understood that other materials, such as biologically active materials (therapeutic agents) may be included within the sac.

The present invention will be further described with respect to the following example; however, the scope of the invention is not to be limited thereby:

EXAMPLE

Dissolve an equimolar mixture of 2-hexadecoxy-3-octadecoxypropyl-(2'-(trimethylammonium) ethyl)-phosphenate, prepared as described in the literature, and cholesterol in a 9:1 mixture of chloroform and methanol. Evaporate to dryness. Add a solution of sulforhodamine B in water (0.1M) at 60° C., sonicate briefly, and wash several times with a buffer solution of the same osmolarity as the encapsulated dye (310 mosm/kg) to prevent osmoticlysis. The vesicles are filtered through 0.4 u filter.

The vesicles may be used in a conventional enzyme immunoassay in which the enzyme marker is a phospholipase, with such vesicles being substituted for the substrate.

Numerous modifications and variations of the present invention are possible in light of the above teachings and, therefore, within the scope of the appended claims, the invention may be practiced otherwise than as particularly described.

What is claimed is:
1. A product, comprising:
a liposome, said liposome being formed from a compound having the following structural formula:

wherein X is a hydrophobic radical of the formula:

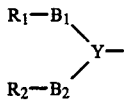

wherein
each of $B_1$ and $B_2$ is selected from the group consisting of —O— and $CH_2$;
$R_1$ and $R_2$ are each selected from the group consisting of hydrocarbon radicals having at least 11 carbon atoms, and
Y is a hydrocarbon radical having from 1 to 5 carbon atoms;
A is a hydrophilic radical; and
L is selected from the group consisting of:

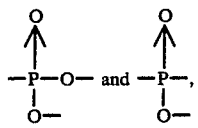

wherein the negative valence of L is satisfied by a positive valence in said hydrophilic radical.

2. The product of claim 1 wherein the liposome includes a detectable marker.

3. The product of claim 2 wherein A is

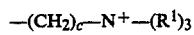

wherein C is 2–10 and each R is selected from the group consisting of hydrogen and an aliphatic hydrocarbon radical having from 1 to 8 carbon atoms.

4. The product of claim 3 wherein A is selected from the group consisting of $$-CH_2-N^+(CH_3), \text{ and}$$

$$-CH_2-CH_2-N^+H_3.$$

5. The product of claim 4 wherein X is

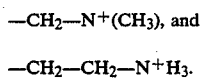

wherein $R_1$ and $R_2$ are each saturated aliphatic hydrocarbons having at least 11 carbon atoms.

6. The product of claim 3 wherein the detectable marker is a chromogen.

7. In an assay for an analyte employing a tracer having an enzyme label wherein there is produced in the assay a bound fraction comprising tracer bound to a binder and a free tracer fraction, the improvement comprising:
contacting at least one of the bound and free tracer fraction with a liposome as defined in claim 3, said enzyme label being an enzyme which is bound by said liposome and determining detectable of marker liposome bound to the tracer of at least one of the bound and free tracer fractions as a measure of analyte.

8. The assay of claim 7 wherein the enzyme label is a phospholipase.

9. A reagent kit for determining an analyte, comprising:
a package, said package including a tracer containing an enzyme label; and a liposome as defined in claim 3, said enzyme label being an enzyme which bound by said liposome.

10. The reagent kit of claim 9 wherein the enzyme label is a phospholipase.

11. In an assay for analyte employing a tracer having an enzyme label wherein there is produced in the assay a bound fraction comprising tracer bound to a binder and a free tracer fraction, the improvement comprising:
contacting at least one of the bound and free tracer fraction with a liposome, said liposome being formed from a compound having the following structural formula:

X—L—A wherein
X is a hydrophobic radical;
A is a hydrophilic radical; and
L is selected from the group consisting of:

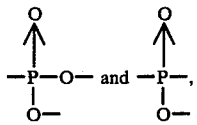

wherein the negative valence of L is satisfied by a positive valence in said hydrophilic radical, said liposome also including a detectable marker, said enzyme label being an enzyme which is bound by said liposome; and determining detectable marker of liposome bound to the tracer of at least one of the bound and free tracer fractions as a measure of analyte.

12. The assay of claim 11 wherein the enzyme label is a phospholipase.

13. The assay of claim 11 wherein A is

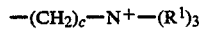

wherein C is 2–10 and each $R^1$ is selected from the group consisting of hydrogen and an aliphatic hydrocabon radical having from 1 to 8 carbon atoms.

14. The assay of claim 13 wherein the enzyme label is a phospholipase.

15. The assay of claim 14 wherein X is:

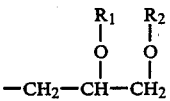

wherein $R_1$ and $R_2$ are each saturated aliphatic hydrocarbons having at least 11 carbon atoms.

16. A reagent kit for determining an analyte, comprising:
a package, said package including a tracer containing an enzyme label, and a liposome, said liposome being formed from a compound having the following structural formula:

X—L—A wherein

X is a hydrophobic radical;
A is a hydrophilic radical; and
L is selected from the group consisting of:

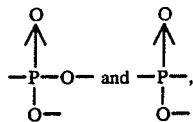

wherein the negative valence of L is satisfied by a positive valence in said hydrophilic radical, said liposome also including a detectable marker, said enzyme label being an enzyme which is bound by said liposome.

17. The reagent kit of claim 16 wherein the enzyme label is a phospholipase.

18. The reagent kit of claim 16 wherein A is:

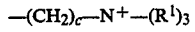

wherein C is 2-10 and each $R^1$ is selected from the group consisting of hydrogen and an aliphatic hydrocarbon radical having from 1 to 8 carbon atoms.

* * * * *